(12) United States Patent
Mao

(10) Patent No.: US 9,314,199 B2
(45) Date of Patent: Apr. 19, 2016

(54) DISPOSABLE STERILE RETRACTING BLOOD TAKING NEEDLE

(75) Inventor: Chunyuan Mao, Shanghai (CN)

(73) Assignee: Shanghai Jinta Medical Co., Ltd., Fengjing Town, Jinshan District, Shanghai (CN)

( * ) Notice: Subject to any disclaimer, the term of this patent is extended or adjusted under 35 U.S.C. 154(b) by 0 days.

(21) Appl. No.: 14/356,764

(22) PCT Filed: Dec. 21, 2011

(86) PCT No.: PCT/CN2011/084372
§ 371 (c)(1),
(2), (4) Date: Nov. 24, 2014

(87) PCT Pub. No.: WO2013/078741
PCT Pub. Date: Jun. 6, 2013

(65) Prior Publication Data
US 2015/0105693 A1    Apr. 16, 2015

(30) Foreign Application Priority Data

Dec. 1, 2011    (CN) .......................... 2011 1 0393465

(51) Int. Cl.
*A61B 5/15*    (2006.01)
*A61B 5/153*    (2006.01)

(52) U.S. Cl.
CPC ......... *A61B 5/150633* (2013.01); *A61B 5/1405* (2013.01); *A61B 5/15003* (2013.01);
(Continued)

(58) Field of Classification Search
CPC ................... A61B 5/150641; A61B 5/150648; A61B 5/150656; A61B 5/150717; A61B 5/150732
See application file for complete search history.

(56) References Cited

U.S. PATENT DOCUMENTS 4,631,057 A * 12/1986 Mitchell ............. A61M 5/3243
604/198
4,693,708 A * 9/1987 Wanderer ............... A61B 5/153
604/198
(Continued)

FOREIGN PATENT DOCUMENTS

CN        1089511        7/1994
CN        2484969 Y      4/2002
(Continued)

OTHER PUBLICATIONS

GB Application No. 1409935.2, filed Jun. 4, 2014.
(Continued)

*Primary Examiner* — Michael C Stout
(74) *Attorney, Agent, or Firm* — Andrus Intellectual Property Law, LLP

(57) ABSTRACT

A disposable sterile retracting blood taking needle consists of an end cover, a protective sleeve, a needle guard, a needle, a needle hub, a core rod. An outer sleeve, a piston, a sheath and a blood taking needle. The piston is arranged in a clamping groove of the core rod; the outer sleeve is sleeved on the core rod and the piston; the piston and the outer sleeve are in interference fit; inner holes of the needle, the needle hub, the core rod and the blood taking needle are communicated; the core rod and the outer sleeve are made of transparent materials; blood backflow is judged by blood flowing in a passage in the core rod; and after blood taking is completed, a medical worker presses a blood taking position of the blood taking needle with one hand, presses the outer sleeve with a finger of the other hand and pulls the needle guard to move back with other fingers of the other hand, so that a snap ring of the core rod enters a slot of the outer sleeve and is locked, and the blood taking needle is hidden in a cylinder of the outer sleeve, and thus the aim of safety is fulfilled.

1 Claim, 10 Drawing Sheets

(52) U.S. Cl.
CPC ......... *A61B5/1535* (2013.01); *A61B 5/150259* (2013.01); *A61B 5/150351* (2013.01); *A61B 5/150389* (2013.01); *A61B 5/150496* (2013.01); *A61B 5/150572* (2013.01); *A61B 5/150595* (2013.01); *A61B 5/150641* (2013.01); *A61B 5/150656* (2013.01); *A61B 5/150732* (2013.01); *A61B 5/150916* (2013.01); *A61B 5/150549* (2013.01); *A61B 5/150564* (2013.01); *A61B 5/150587* (2013.01); *A61B 5/150603* (2013.01); *A61B 5/150717* (2013.01)

(56) References Cited

U.S. PATENT DOCUMENTS

| | | | | |
|---|---|---|---|---|
| 4,731,059 A * | 3/1988 | Wanderer | A61B 5/1405 | 600/577 |
| 4,758,231 A * | 7/1988 | Haber | A61B 5/150496 | 600/576 |
| 4,923,446 A * | 5/1990 | Page | A61M 5/3243 | 604/198 |
| 4,935,012 A * | 6/1990 | Magre | A61B 5/1433 | 604/192 |
| 5,011,479 A * | 4/1991 | Le | A61M 5/3271 | 604/198 |
| 5,057,087 A * | 10/1991 | Harmon | A61M 5/3243 | 604/110 |
| 5,066,287 A * | 11/1991 | Ryan | A61B 5/1437 | 600/576 |
| 5,295,975 A * | 3/1994 | Lockwood, Jr. | A61B 5/1405 | 604/198 |
| 5,338,310 A * | 8/1994 | Lewandowski | A61B 5/1438 | 604/110 |
| 5,407,431 A * | 4/1995 | Botich | A61B 5/154 | 604/110 |
| 5,423,758 A * | 6/1995 | Shaw | A61B 5/1438 | 600/576 |
| 5,647,849 A * | 7/1997 | Kalin | A61M 5/3243 | 604/111 |
| 5,687,740 A * | 11/1997 | Sheridan | A61B 5/1438 | 600/573 |
| 5,718,239 A * | 2/1998 | Newby | A61B 5/1438 | 600/576 |
| 5,735,823 A * | 4/1998 | Berger | A61M 5/3243 | 604/192 |
| 6,443,929 B1 * | 9/2002 | Kuracina | A61B 5/150572 | 604/192 |
| 6,471,677 B2 * | 10/2002 | Domici, Jr. | A61M 5/3271 | 604/110 |
| 6,537,257 B1 * | 3/2003 | Wien | A61M 5/3202 | 604/198 |
| 6,702,786 B2 * | 3/2004 | Olovson | A61M 5/3202 | 604/192 |
| 6,989,001 B2 * | 1/2006 | Chen | A61M 5/50 | 128/919 |
| 2002/0165498 A1 | 11/2002 | Ward, Jr. | | |
| 2003/0050608 A1 | 3/2003 | Brown | | |
| 2006/0229554 A1 * | 10/2006 | Lou | A61M 5/322 | 604/110 |
| 2009/0204026 A1 * | 8/2009 | Crawford | A61B 5/1422 | 600/576 |
| 2010/0286604 A1 * | 11/2010 | Shaw | A61M 5/3234 | 604/68 |
| 2010/0331726 A1 | 12/2010 | Steube et al. | | |

FOREIGN PATENT DOCUMENTS

| | | |
|---|---|---|
| CN | 1383899 | 12/2002 |
| CN | 101361661 | 2/2009 |
| CN | 201735028 | 2/2011 |
| CN | 102160793 | 8/2011 |
| CN | 102525488 | 7/2012 |

OTHER PUBLICATIONS

English translation of Chinese Office Action issued Jun. 3, 2013, in CN 201110393465.4.
Written Opinion issued Sep. 6, 2012, for PCT/CN2011/084372.
International Search Report for PCT/CN2011/084372 dated Aug. 20, 2012.

* cited by examiner

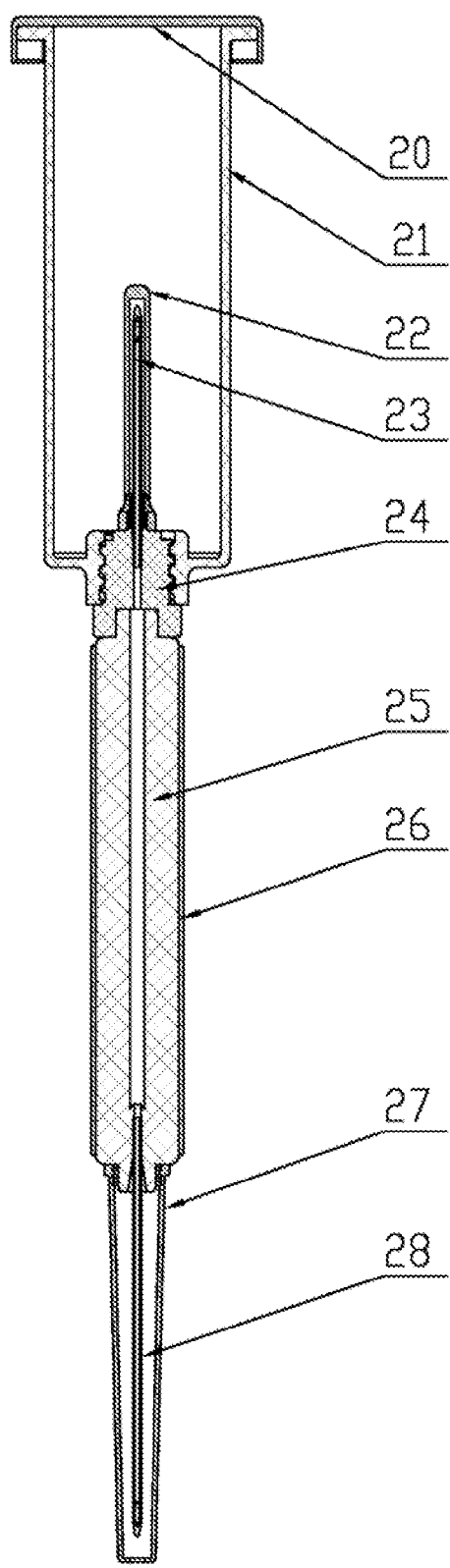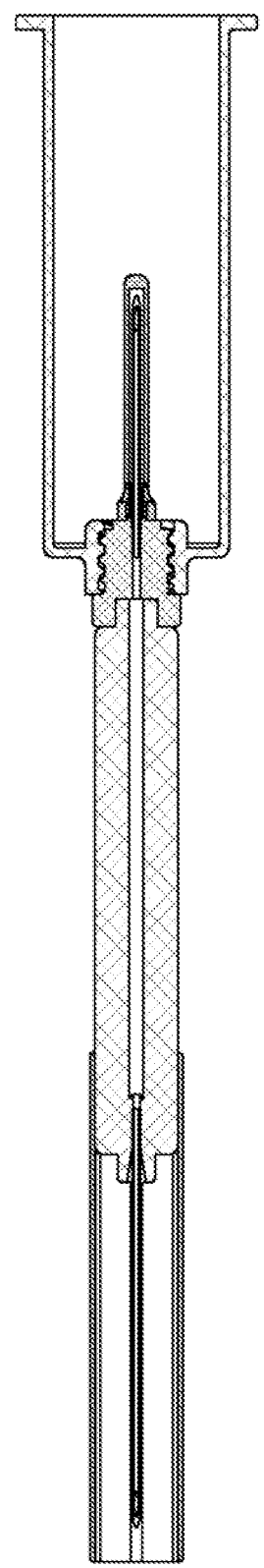
Figure 12                    Figure 13

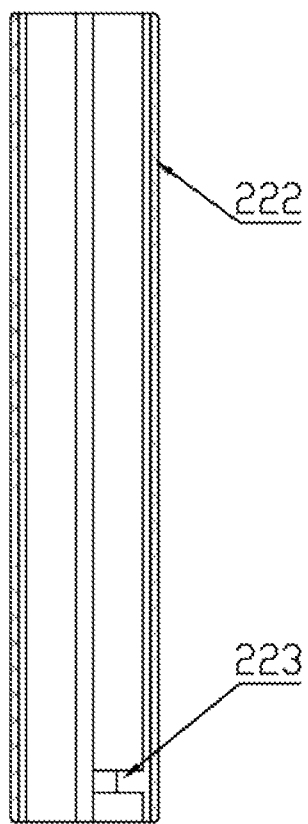 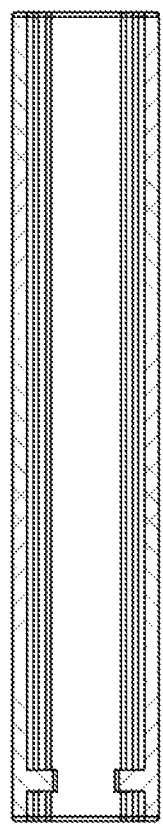 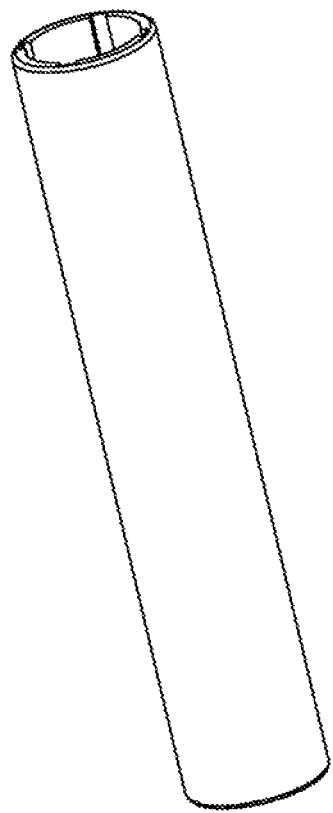
Figure 19　　　　Figure 20　　　　Figure 21
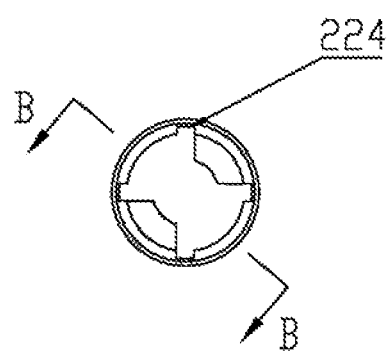
Figure 22

DISPOSABLE STERILE RETRACTING BLOOD TAKING NEEDLE

CROSS REFERENCE TO RELATED APPLICATION

The present application is the U.S. national stage application of International Application PCT/CN2011/084372, filed Dec. 21, 2011, which international application was published on Jun. 6, 2013, as International Publication WO2013/078741. The International Application claims priority of Chinese Patent Application 201110393465.4, filed Dec. 1, 2011. the contents of which are incorporated herein by reference in their entireties.

FIELD OF INVENTION

The present invention relates to a blood taking needle, especially the needle can be retracted into an outer sleeve after taking blood, which prevent people being punctured again, the blood taking needle is a retracting safe blood taking needle.

PRIOR ARTS

Blood taking needle is one of the best-selling medical devices in the world. However, it is concerned that the injury accidents caused by the broken of the needle or the improper operation of the medical personnel happen millions of times a year in the hospitals around the world. According to the data of the American Medical Association, only in America, the injury accidents that the medical personnel are punctured by the blood taking needle happen almost one million times every year, at least a thousand people get infected with hepatitis B, hepatitis C and AIDS carried by the needle. The emergency treatments for the medical personnel which are punctured by the broken needle cost 3000 dollars per capita.

The medical risk of using the custom blood taking needle is no lower than the risk of using the syringe, and we can see in the near future that the governments will legislate for the safe blood taking. In 2000, President Clinton signed the federal Needlestick Safety and Prevention Act (NSPA). The act ruled that the safe syringes should replace the custom syringes which have security risks in the clinical medicine field.

The domestic and foreign companies have devoted to the research of the safe blood taking medical devices, now there are a variety of safe blood taking needles in the market, the safe blood taking needles have been accepted, but there is still a long way for the popularization of the safe blood taking needles to go. The safe blood taking needles in the market currently have lots of defects: the first is the high cost of production, the second is the complex production process, the third is that the production quality cannot be guaranteed, the fourth is the complex operation of the medical personnel and the fifth is the security cannot be guaranteed.

The present invention adopts new design which breaks the traditional ideas to overcome the defects. The objective of the present invention is to overcome the defects of the current blood taking devices. The present invention achieves the low cost of production, simple production process, quality assurance, simple operation of the medical personnel and the security assurance.

CONTENT OF THE PRESENT INVENTION

Invention 1

The present invention consists of an end cover, a protective sleeve, a needle guard, a needle, a needle hub, a core rod, an outer sleeve, a piston, a sheath and a blood taking needle.

The technical solution 1 applied to solve the technical problem is that: the blood taking needle is arranged in a pinhole, glue is applied in a glue hole to tighten the connection between the blood taking needle and the core rod; a column is arranged in a cylinder of the piston, the two end faces of the piston are limited by an groove end face and another groove end face, the fit between the cylinder and the column is an interference fit; the piston is arranged in the front of the cylinder, the fit between a lug ring of the piston and the cylinder is an interference fit, the core rod is arranged inside a cylinder, the fit between the core rod and the outer sleeve is a transition fit, the fit between a snap ring and a lock bevel is an interference fit only when the snap ring runs to the position of the limit bevel, the cylindrical head or the core rod passes through a hole of the outer sleeve; the inner holes of the needle, the needle hub and the blood taking needle are communicated.

The technical solution 2 applied to solve the technical problem is that: the core rod consists of a duct and a joint; the duct is made of flexible materials; the fit between the duct and a cone of the needle hub, and the fit between the duct and a cone of the joint are both interference fits which also can be achieved by the slot structure of the port shown in FIG. 10; the inner holes of the needle, the needle hub, the duct, the joint and the blood taking needle are communicated.

The technical solution 3 applied to solve the technical problem is that: a circular column and a cone are arranged on the rear of the core rod, the cone is arranged in the circular column, a circular column, a lug and a path are arranged on the middle of the core rod, the path is arranged inside a circular column, the lug is arranged on the circular column; the snap ring, the groove end face, the column, the groove end face, the pinhole, the glue hole and the cylindrical head are arranged on the front of the core rod, the front, middle and rear inner holes of the core rod are communicated; the lug ring of the piston surrounds a circular column, an inner hole is arranged in the center of the circular column; a guide hole, an end face, a handle, a limit ring, and a limit bevel are arranged on the rear of the outer sleeve, the diameter of the limit ring is smaller than the diameter of the cylinder; the middle of the outer sleeve is a hollow cylindrical tube, on the front of the outer sleeve there are a mesa and a hole; a slot and a lug are arranged on the rear of the outer sleeve, when the snap ring is pulled into the slot, the limit bevel and the lug prevent the outer sleeve from moving forward and backward.

The technical solution 4 applied to solve the technical problem is that: the core rod and the outer sleeve are made of transparent materials, the blood backflow can be detected by observing the flowing of the blood in the path of the core rod.

The technical solution 5 applied to solve the technical problem is that: the silicone lubricant is sprayed on the surface of the piston and the outer sleeve.

The technical solution 6 applied to solve the technical problem is that: the core rod, the outer sleeve, the piston, the sheath and the blood taking needle are fitted together, the core rod connects with a duct of a blood sampling bag for blood taking.

Invention 2

The present invention consists of an end cover, a sheath, a needle guard, a needle, a needle hub, a core rod, an outer sleeve, a sheath and a blood taking needle.

The technical solution 1 applied to solve the technical problem is that: a column of the core rod is arranged in a hole of the needle hub, the outer sleeve is set outside the core rod, the lug of the core rod is arranged in the slot of the outer sleeve.

The technical solution 2 applied to solve the technical problem is that: a mesa is fitted on a boss column to form an interference fit, the through-hole of the core rod consists of the path and the glue hole; the lug of the core rod is arranged on the boss column, a column, a mesa, a slot, a mesa, wherein the mesa and the other mesa are located at the two sides of the slot, a tapered transition is applied at the joint of the mesa and the column, as well as at the joint of the mesa and the column.

The technical solution 3 applied to solve the technical problem is that: the outer sleeve is a hollow cylinder, slots are arranged on the inner surface of the hollow cylinder, and the mesa is a lug on the inner surface of the hollow cylinder.

BRIEF DESCRIPTION OF THE DRAWINGS

FIG. 12 is a view showing the structure of the safe blood taking means in invention 2.
FIG. 13 is a view showing the structure of the safe blood taking means in invention 2, which is in a retracting state.
FIG. 19 is a view showing the structure of the outer sleeve of the safe blood taking means in invention 2.
FIG. 20 is a sectional view showing the structure of the FIG. 22 in the B-B direction.
FIG. 21 is a stereo view showing the structure of the outer sleeve of the safe blood taking means in invention 2.
FIG. 22 is a top view of FIG. 19.

Figure 1:
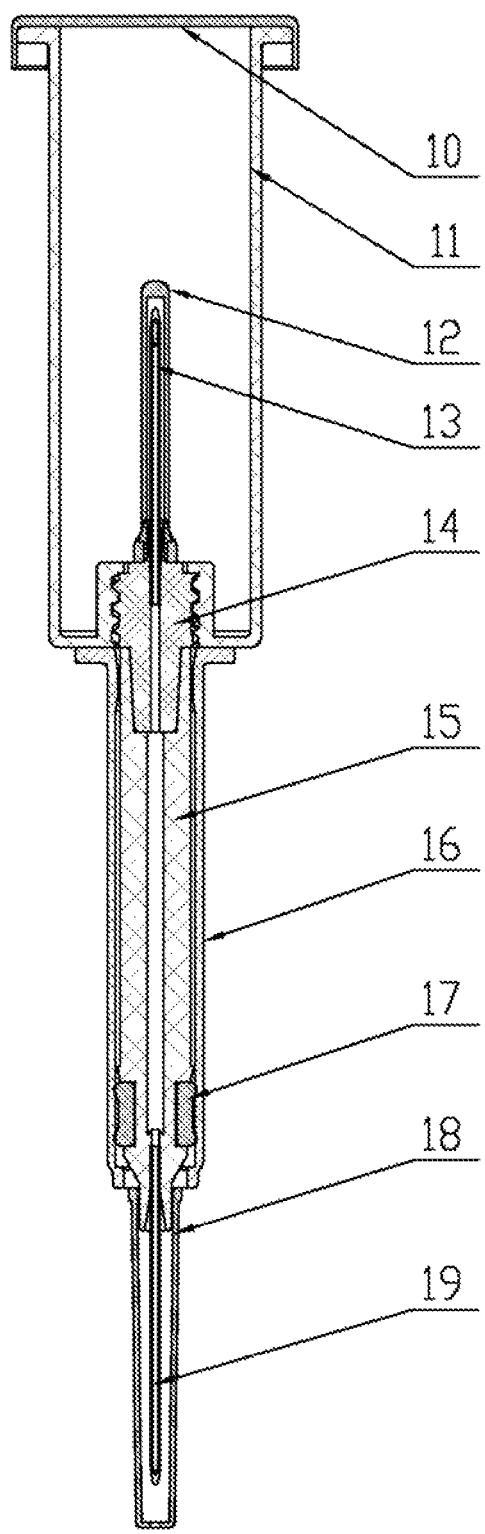
FIG. 1 is a view showing the structure of the safe blood taking means in invention 1.
Figure 2:
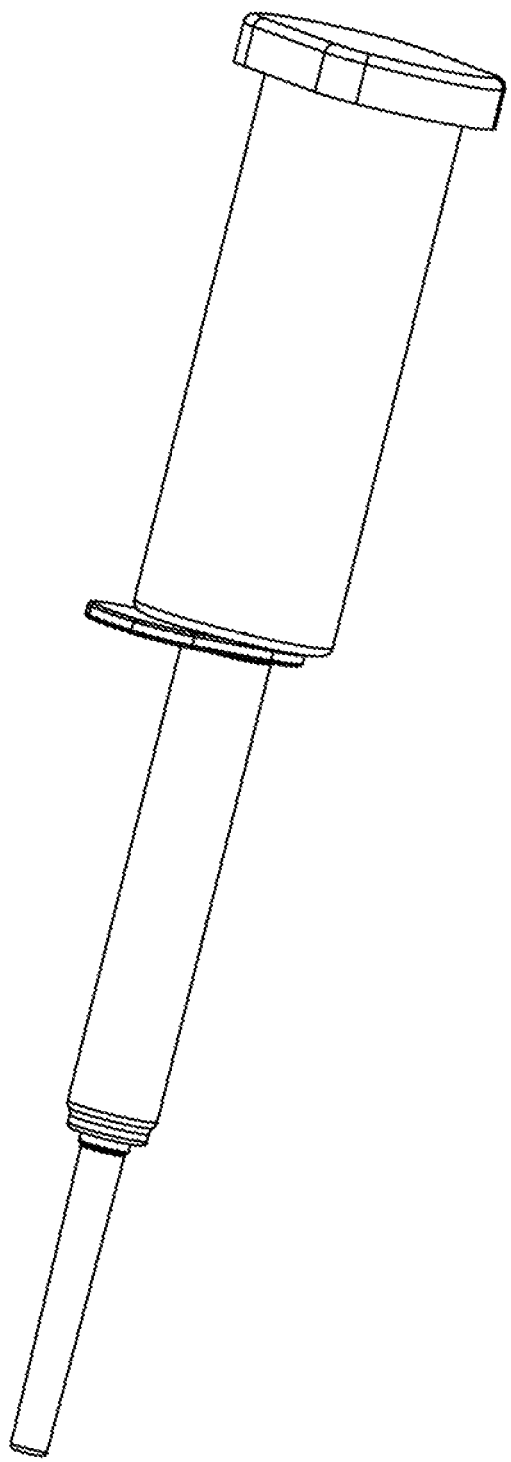
FIG. 2 is a view showing the appearance of the safe blood taking means in invention 1.
Figure 3:
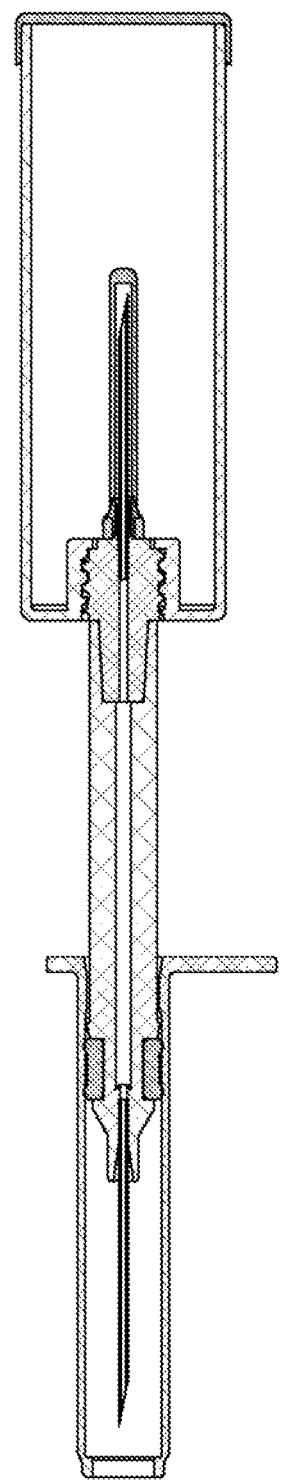
FIG. 3 is a view showing the structure of the safe blood taking means in invention 1, which is in a retracting state.
Figure 4:
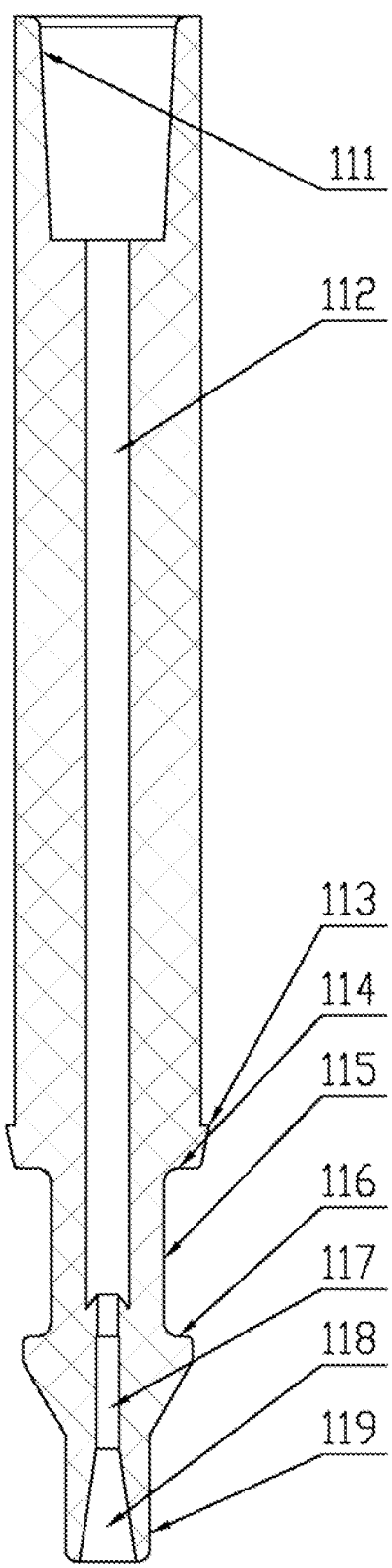
FIG. 4 is a view showing the structure of the core rod of the safe blood taking means in invention 1.
Figure 5:
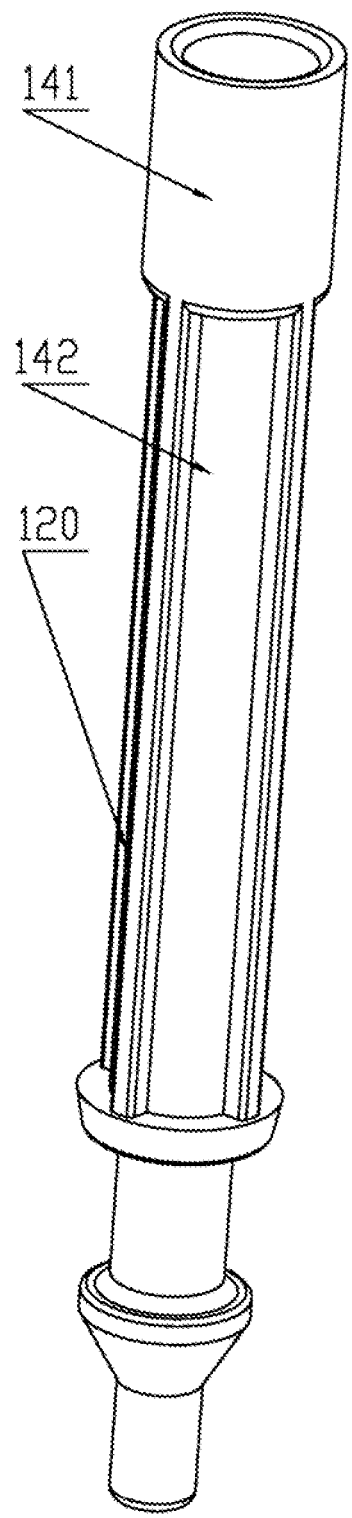
FIG. 5 is a stereo view showing the structure of the core rod of the safe blood taking means in invention 1.
Figures 6, 7:
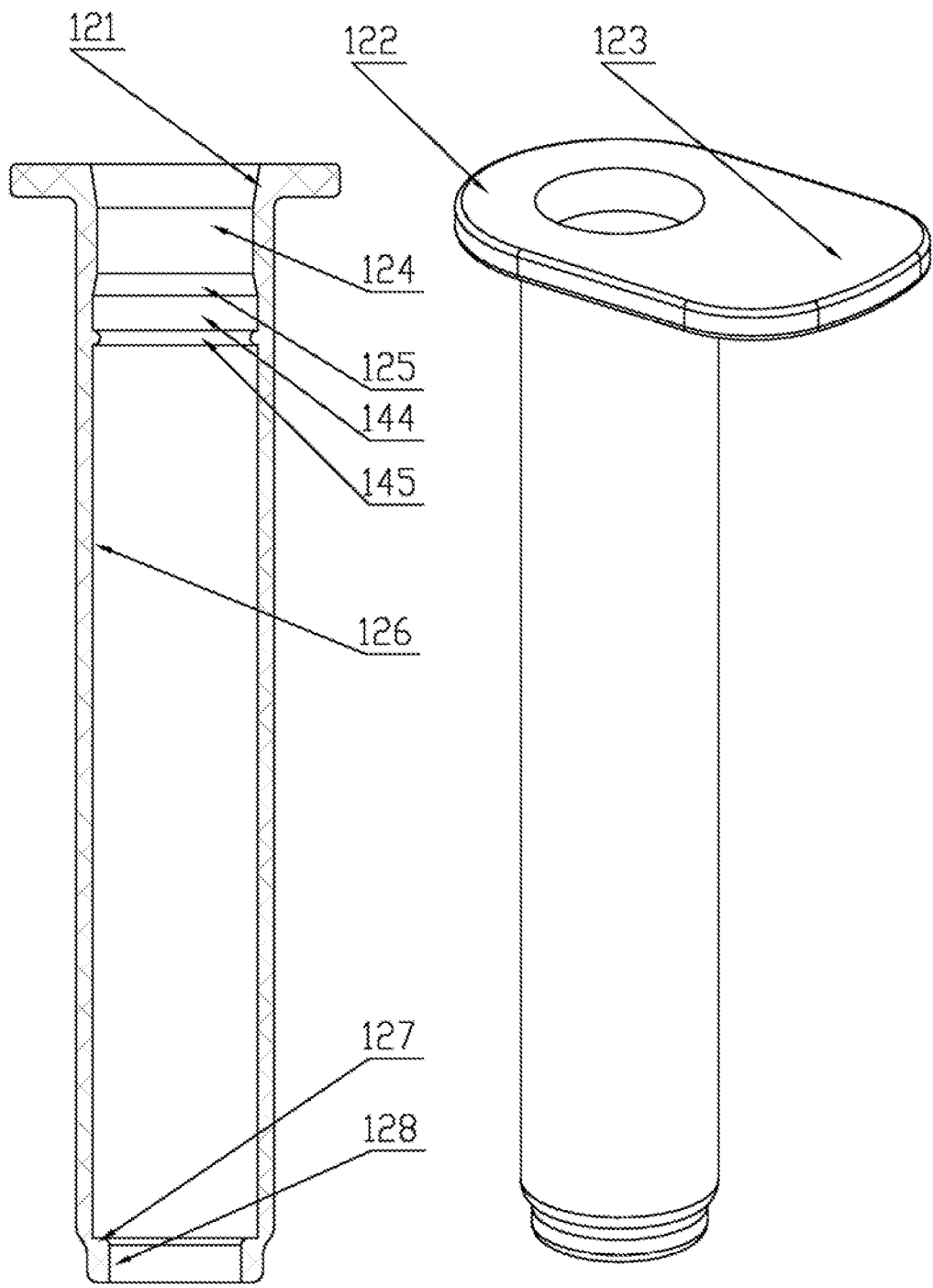
FIG. 6 is a view showing the structure of the outer sleeve of the safe blood taking means in invention 1.
FIG. 7 is a stereo view showing the structure of the outer sleeve of the safe blood taking means in invention 1.
Figure 8:
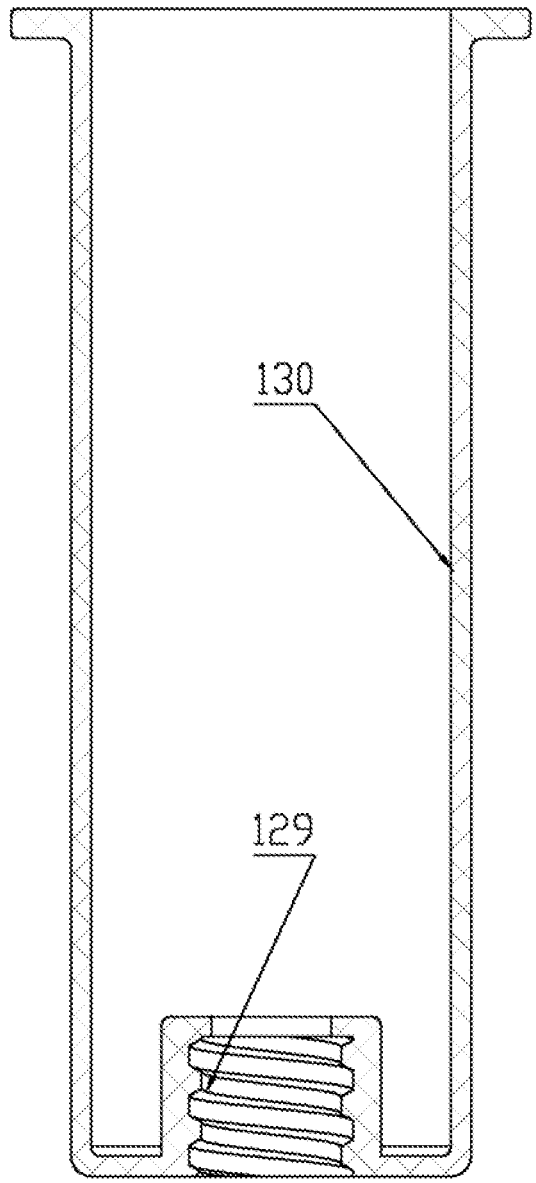
FIG. 8 is a view showing the structure of the protective sleeve of the safe blood taking means in invention 1.
Figure 9:
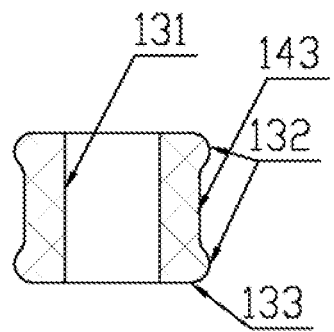
FIG. 9 is a view showing the structure of the piston of the safe blood taking means in invention 1.

Invention 1: 10. end cover; 11. protective sleeve; 12. needle guard; 13. needle; 14. needle hub; 15. core rod; 16. outer sleeve; 17. piston; 18. sheath; 19. blood taking needle; 111. cone; 112. path; 113. snap ring; 114. groove end face; 115. column 116. groove end face; 117. pinhole; 118. glue hole; 119. cylindrical head; 120. lug; 121. guide hole; 122. end face; 123. handle; 124. limit ring; 125. limit bevel; 126. cylinder; 127. mesa; 128. hole; 129. screw hole; 130. cylinder; 131. inner hole; 132. lug ring 133. end face; 134. cone; 135. bolt; 136. port; 137. glue hole; 138. pinhole; 139. duct; 140. joint; 141. circular column; 142. circular column; 143. circular column; 144. slot; 145. lug Invention 2: 20. end cover; 21. protective sleeve; 22. needle guard; 23. needle; 24. needle hub; 25. core rod; 26. outer sleeve; 27. sheath; 28. blood taking needle; 211. needle glue hole; 212. hole; 213. column; 214. boss column; 215. lug; 216. column; 217. path; 218. mesa; 219. slot; 220. mesa; 221. needle glue hole; 222. slot wall; 223. mesa; 224. slot The conventional blood taking needle is well known for us, so parts of the blood taking needle in the invention are described simply below, such as the structure, the assembly relation, the assembly position and the usage method, said parts are similar to conventional blood taking needles is, and the following only describes the key point of the invention in detail, those which are shown clearly in the append figures are also described simply below.

Invention 1:

The blood taking means in present invention consists of an end cover 10, a protective sleeve 11, a needle guard 12, a needle 13, a needle hub 14, a core rod 15, an outer sleeve 16, a piston 17, a sheath 18 and a blood taking needle 19.

The blood taking needle 19 is arranged in a pinhole 117, glue is applied in a glue hole 118 to tighten the connection between the blood taking needle 19 and the core rod 15; a column 115 is arranged in a cylinder 131 of the piston 17, the two end faces 133 of the piston 17 are limited by an groove end face 114 and another groove end face 116, the fit between the cylinder 131 and the column 115 is an interference fit; the piston 17 is arranged in the front of the cylinder 126, the fit between a lug ring 132 of the piston 17 and the cylinder 126 is an interference fit, the silicone lubricant is sprayed on the surface of the piston 17 and the outer sleeve 16 to maintain the stability of the slide thrust, the core rod 15 is arranged inside the cylinder 131, the fit between the core rod 15 and the outer sleeve 16 is a transition fit, the fit between a snap ring 113 and a limit bevel 125 is an interference fit only when the snap ring 113 runs to the position of the limit bevel 125, the cylindrical head 119 of the core rod 15 passes through a hole 128 of the outer sleeve 16; the inner holes of the needle 13, the needle hub 14, the core rod 15 and the blood taking needle 19 are communicated.

The end cover 10 covers the end of the protective sleeve 11; the needle hub 14 is arranged in the screw hole 129; the needle 13 is arranged in the pinhole 138; the glue is applied in the glue hole 137 for bonding; the needle guard 12 is set over the needle 13 and the port 136; a cone 111 of the core rod 15 is set over the cone 134 for tightening connection, the glue is applied for bonding; the sheath 18 is set over the one 111.

A circular column 141 and the cone 111 are arranged on the rear of the core rod 15, the cone 111 is arranged inside the circular column 141, a circular column 141, a circular column 142, a lug 120 and a path 112 are arranged on the middle of the core rod 15, the path 112 is arranged inside the circular column 142, the lug 120 is arranged on the circular column 142; the snap ring 113, the groove end face 114, the column 115, the groove end face 116, the pinhole 117, the glue hole 118 and the cylindrical head 119 are arranged on the front of the core rod 15, the front, middle and rear inner holes of the core rod 15 are communicated.

The lug ring 132 of the piston 17 surrounds a circular column 143, an inner hole 131 is arranged in the center of the circular column 143.

A guide hole 121, an end face 122, a handle 123, a limit ring 124, and a limit bevel 125 are arranged on the rear of the outer sleeve 16, the diameter of the limit ring 124 is smaller than the diameter of the cylinder 126; the middle of the outer sleeve 16 is a hollow cylindrical tube, on the front of the outer sleeve 16 there are a mesa 127 and a hole 128; a slot 144 and a lug 145 are arranged on the rear of the outer sleeve 16, when the snap ring 113 is pulled into the slot 144 after use, the limit bevel 125 and the lug 145 prevent the outer sleeve 16 from moving forward and backward.

Figure 10:
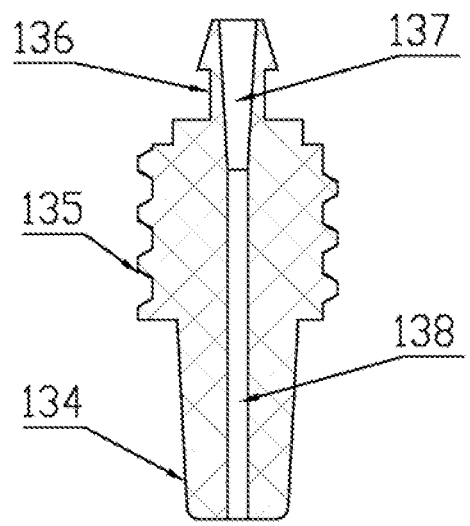
FIG. 10 is a view showing the structure of the needle hub of the safe blood taking means in invention 1.
Figure 11:
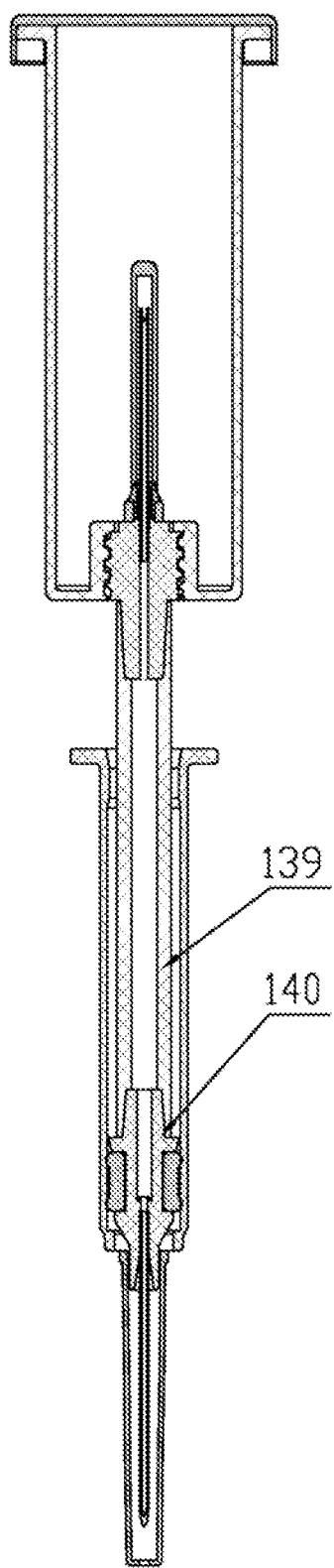
FIG. 11 is a view showing the structure of the safe blood taking means (with an improved core rod) in invention 1.
Figure 15:
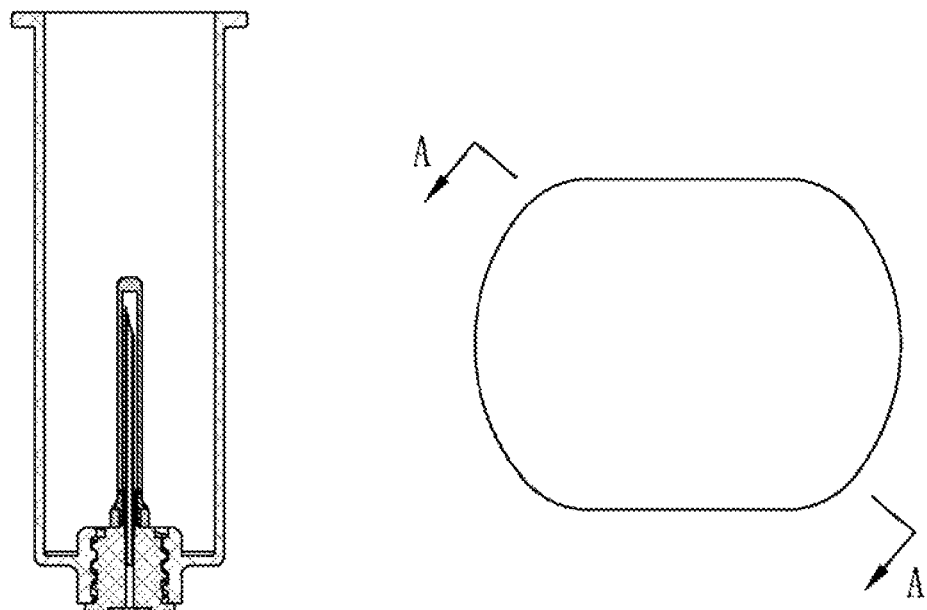
FIG. 15 is a top view of FIG. 12.
Figure 14:
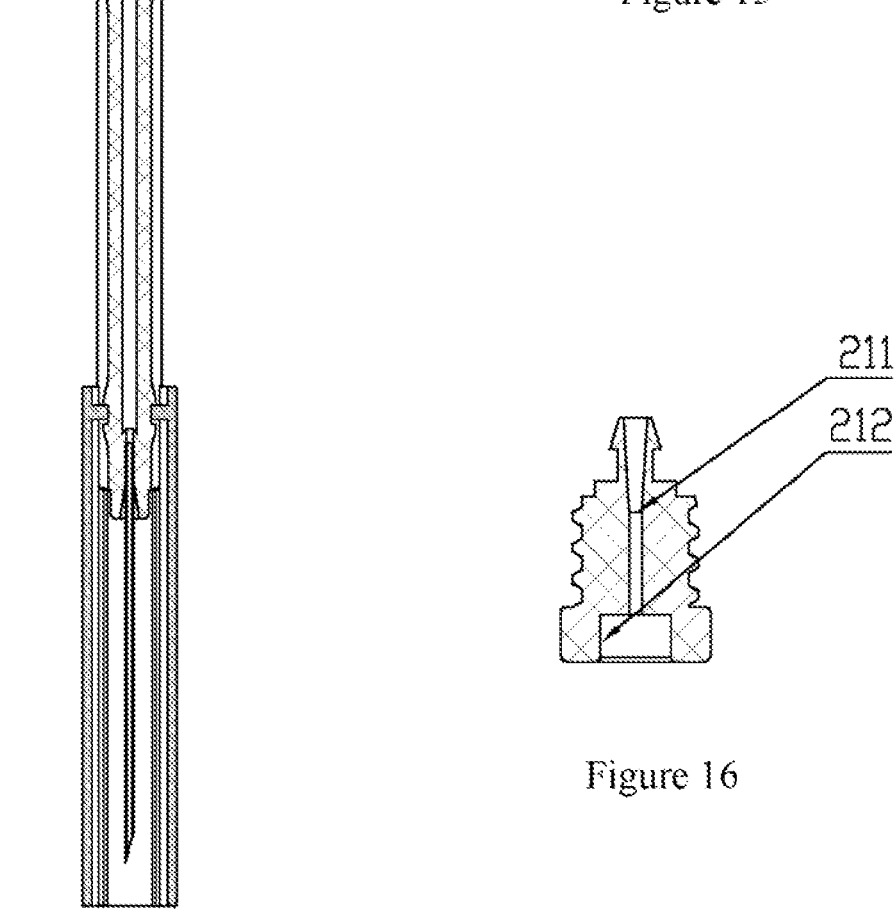
FIG. 14 is a sectional view showing the structure of the FIG. 15 in the A-A direction.
Figure 16:
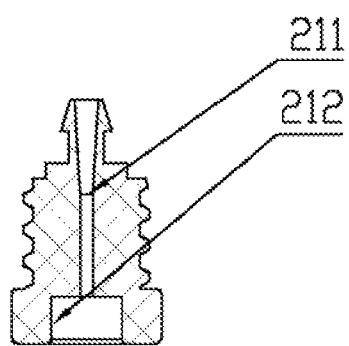
FIG. 16 is a view showing the structure of the needle hub of the safe blood taking means in invention 2.
Figure 17:
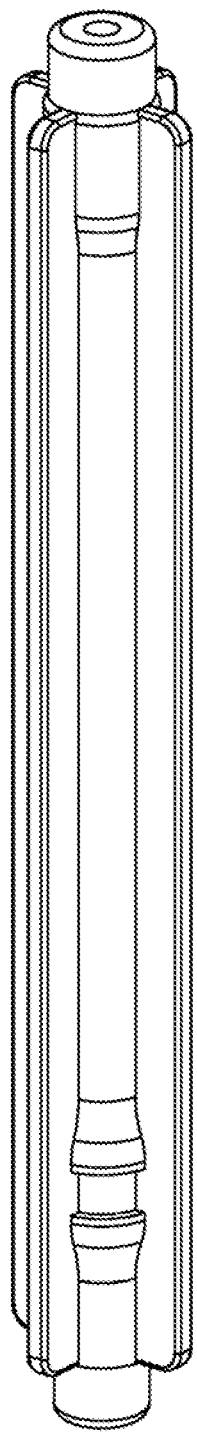
FIG. 17 is a stereo view showing the structure of the core rod of the safe blood taking means in invention 2.
Figure 18:
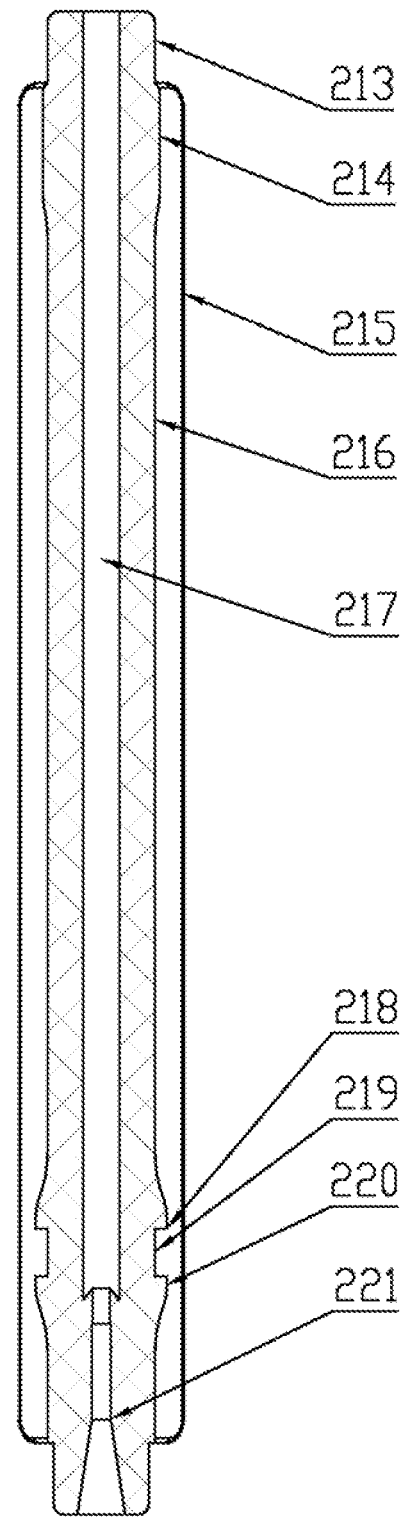
FIG. 18 is a view showing the structure of the core rod of the safe blood taking means in invention 2.

Alternatively, the core rod 15 consists of a duct 139 and a joint 140; the duct 139 is made of flexible materials, so the blood taking needle will not swing with the sway of the rear of the blood taking needle; the fit between the duct 139 and a cone 134 of the needle hub 14, and the fit between the duct 139 and a cone of the joint 140 are both interference fits which also can be achieved by the slot structure of the port 136 shown in FIG. 10; the inner holes of the needle 13, the needle hub 14, the duct 139, the joint 140 and the blood taking needle 19 are communicated.

Invention 2

The blood taking means in present invention consists of an end cover 20, a sheath 21, a needle guard 22, a needle 23, a needle hub 24, a core rod 25, an outer sleeve 26, a sheath 27 and a blood taking needle 28. The invention is another technical solution bases on the invention 1.

A column 213 of the core rod 25 is arranged in a hole 212 of the needle hub 24, the outer sleeve 26 is set outside the core rod 25, the lug 215 of the core rod 25 is arranged in the slot 224 of the outer sleeve 26. A mesa 223 is fitted on a boss column 214 to form an interference fit, relative movement occurs between the outer sleeve 26 and the core rod 25 after taking blood until the mesa 223 being locked in a slot 219, and a through-hole of the core rod 25 consists of the path 217 and the glue hole 221.

The lug 215 of the core rod 25 is arranged on the boss column 214, a column 216, a mesa 218, a slot 219, a mesa 220, wherein the mesa 218 and the mesa 220 are located at the two sides of the slot 219, a tapered transition is applied at the joint of the mesa 218 and the column 216, as well as at the joint of the mesa 220 and the column 216.

The outer sleeve 26 is a hollow cylinder, slots 224 are arranged on the inner surface of the hollow cylinder, and the mesa 223 is a lug on the inner surface of the hollow cylinder.

DETAILED DESCRIPTION OF THE PREFERRED EMBODIMENT

Embodiment 1

When using, the medical personnel takes the safe blood taking needle out of the package, and unplug the end cover 10, then unplug the protective sleeve 18, at last the medical personnel can take blood according to the blood taking procedure when using the custom blood taking needle. The core rod 15 and the outer sleeve 16 are made of transparent materials, it can be judged whether the blood taking needle 19 is inserted into the blood vessel correctly by observing the blood flow in the path 112 of the core rod 15. Then the blood collection tube should be inserted into the needle guard 12 and the pin 13 is therefore entered into the blood collection tube for blood taking. The blood collection tube should be unplugged when the blood collection tube is filled with blood, another blood collection tube should be inserted into the needle guard 12 for the entrance of the pin 13 if more blood is needed. After blood taking, the medical personnel should hold the blood taking position of the blood taking needle 19 with one hand, hold the outer sleeve 16 with one finger of the other hand, and push the needle guard 12 backward with other fingers, the snap ring 113 of the core rod 15 therefore runs into the slot 144 to prevent the relative movement between the core rod 15 and the outer sleeve 16, and finally the blood taking needle 19 is hidden in the cylinder 126 of the outer sleeve 16, and the aim of safety is fulfilled. Afterwards the medical personnel can throw the blood taking needle into the trash can.

During the blood taking or before the blood taking, the friction force between the piston 17 and the outer sleeve 16 does prevent the relative movement between the outer sleeve 16 and the core rod 15.

The core rod 15, the outer sleeve 16, the piston 17, the sheath 18 and the blood taking needle 19 are fitted together, the core rod 15 connects with a duct of a blood sampling bag for blood taking.

Embodiment 2

When using, the medical personnel takes the safe blood taking needle out of the package, and unplug the end cover 20, then unplug the protective sleeve 27, at last the medical personnel can take blood according to the blood taking procedure when using the custom blood taking needle. The core rod 25 and the outer sleeve 26 are made of transparent materials, it can be judged whether the blood taking needle 28 is inserted into the blood vessel correctly by observing the blood flowing in the path 217 of the core rod 25. Then the blood collection tube should be inserted into the needle guard 22 and the pin 23 is therefore entered into the blood collection tube for blood taking. The blood collection tube should be unplugged when the blood collection tube is filled with blood, another blood collection tube should be inserted into the needle guard 22 for the entrance of the pin 23 if more blood is needed. After blood taking, the medical personnel should hold the blood taking position of the blood taking needle 28 with one hand, hold the outer sleeve 26 with one finger of the other hand, and push the needle guard 22 backward with other fingers, the mesa 223 of the outer sleeve 26 therefore runs into the slot 219 to prevent the relative movement between the core rod 25 and the outer sleeve 26, and finally the blood taking needle 28 is hidden in the cylinder of the outer sleeve 26, and the aim of safety is fulfilled. Now the medical personnel can throw the blood taking needle into the trash can.

During the blood taking or before the blood taking, the friction force between the lug 215 of the core rod 25 and the slot 224 of the outer sleeve 26, together with the friction force between the lug column 214 of the core rod 25 and the mesa 223 of the outer sleeve 26 do prevent the relative movement between the outer sleeve 26 and the core rod 25.

It is to be understood that the foregoing description of two preferred embodiments is intended to illustrate, and not limit. Various modifications and variations may occur to those skilled in the art without departing from the true spirit and scope of the invention, all such modifications and variations are intended to be included herein within the scope of this disclosure and protected by the following claims.

What is claimed is:

1. A disposable sterile retracting safe blood taking needle, which consists of an end cover, a protective sleeve, a needle guard, a needle, a needle hub, a core rod, an outer sleeve, a sheath and a blood taking needle, wherein a column on a proximal end of the core rod is arranged in a hole of the needle hub, the outer sleeve is set outside the core rod, a lug of the core rod is arranged in a second slot of the outer sleeve; wherein a third mesa of the outer sleeve is fitted on a boss column on the proximal end of the core rod to form an interference fit, a through-hole of the core rod consists of a path and a glue hole, the blood taking needle is arranged in the glue hole, glue is applied in the glue hole to tighten the connection between the blood taking needle and the core rod; the lug of the core rod is arranged on the boss column on the proximal end of the core rod, a column of the core rod, a first mesa of the core rod, a first slot of the core rod, a second mesa of the core rod, the first mesa and the second mesa are arranged on the two sides of the first slot, a tapered transition is applied at the joint of the first mesa and the column, as well as at the joint of the second mesa and the column; wherein the outer sleeve is a hollow cylinder, the second slot is arranged on the inner surface of the hollow cylinder, and the third mesa is a lug on the inner surface of the hollow cylinder, the third mesa is used for running into the first slot to prevent the relative movement between the core rod and the outer sleeve; during blood taking or before blood taking, the relative movement between the outer sleeve and the core rod is prevented by the friction force between the lug of the core rod and the second slot of the outer sleeve and the friction force between the boss column of the core rod and the third mesa of the outer sleeve; and further wherein the boss column on the proximal end of the core rod has a proximal end that coincides with a proximal end of the lug.

* * * * *